United States Patent [19]
Whitehead

[11] 3,941,479
[45] Mar. 2, 1976

[54] USE OF MODULATED STIMULUS TO IMPROVE DETECTION SENSITIVITY FOR SIGNALS FROM PARTICLES IN A FLOW CHAMBER

[75] Inventor: Frank R. Whitehead, Arlington Heights, Ill.

[73] Assignee: G. D. Searle & Co., Skokie, Ill.

[22] Filed: Sept. 26, 1974

[21] Appl. No.: 509,360

[52] U.S. Cl. .................. 356/102; 356/39; 356/103; 356/181; 235/151.3; 324/71 CP
[51] Int. Cl.² G01N 15/02; G01N 33/16; G01J 3/46
[58] Field of Search .......... 356/102, 103, 104, 181, 356/39; 250/574, 575; 235/151.3; 324/71 CP

[56] References Cited
UNITED STATES PATENTS

| | | | |
|---|---|---|---|
| 3,680,961 | 8/1972 | Rudd | 356/102 |
| 3,819,270 | 6/1974 | Huschfeld | 358/103 |
| 3,830,568 | 8/1974 | Allen | 356/102 |

Primary Examiner—Alfred E. Smith
Assistant Examiner—Conrad J. Clark
Attorney, Agent, or Firm—Walter C. Ramm; Charles H. Thomas, Jr.; Peter J. Sgarbossa

[57] ABSTRACT

Method and apparatus for analyzing blood or other biological fluids containing cells or particles of interest by passing them sequentially through a narrow flow chamber where a repetitive physical stimulus, such as a plurality of beams of light, is spaced at intervals to form a code along the length of the flow chamber to elicit responses from the particles. These responses are then decoded and used to classify the particles according to type.

13 Claims, 9 Drawing Figures

USE OF MODULATED STIMULUS TO IMPROVE DETECTION SENSITIVITY FOR SIGNALS FROM PARTICLES IN A FLOW CHAMBER

This invention relates to a method and apparatus for the analysis of blood or other biological fluids in which small particles, such as single cells, are detected and classified. The invention provides a means of increasing the detection sensitivity for determining the response of particles to a physical stimulus, such as light, when the particles are passed through a narrow flow chamber. A typical example would be in measuring the intensity of fluorescent emission from stained blood cells.

Since the particles are passed one by one, and usually quite rapidly, thru the flow chamber, the response signal is often so weak that adequate detection and measurement is difficult. However, if the stimulus is repetitively, and periodically applied, and the successive responses appropriately detected, then it is possible to add successive responses for each individual particle and obtain a single large response which is more suitable for detection and classification of the number and types of particles present in the sample.

BACKGROUND OF THE INVENTION

Analysis of cells, such as blood cells, may be accomplished by staining the cells with a fluorescent dye and then detecting a fluorescent emission as individual cells pass through a narrow illuminated flow chamber. U.S. Pat. Nos. 3,788,744 and 3,819,270 illustrate conventional techniques and U.S. Pat. No. 3,788,744 describes apparatus for such photoanalysis. This type of photoanalysis is usually performed on several million particles in any particular sample. Since it is always desirable for the complete sample to be measured in only a few minutes, the measurement time allowed for a single particle is in the order of microseconds. As a result, the total integrated signal output from a photodetector responsive to the fluorescent emissions of individual cells is quite weak. If a more substantial signal is required in order to discriminate between different classes of particles, it is necessary to increase the measurement time by reducing the flow rate of particles through the flow chamber. Alternatively, the length of the measurement chamber may be increased and the particle concentration diluted to prevent the possibility that two particles will be in the measurement area of the flow chamber simultaneously. In either case, the total time for analysis of the entire sample is increased. The same problem exists whether the cell counter used is designed for photometric analysis, or whether it operates on a principle of detecting differences other than fluorescent emission. For example, commercial blood cell counters are available which operate on the principle of distinguishing between cells on the basis of electrical conductivity, light scattering, light blockage, or electrical capacitance. U.S. Pat. No. 3,811,841 describes a system employing light blockage in cell detection.

SUMMARY OF THE INVENTION

An object of the present invention is to provide a flow chamber measurement device incorporating pulse code techniques. Practice of the invention leads to increased sensitivity and higher counting rates than is currently possible with conventional systems.

It is a further object of the invention to provide increased measurement sensitivity without a corresponding increase in the illumination or other physical stimulus applied to the measured cells. The most obvious way of increasing sensitivity in photometric analysis of blood cells would be to simply increase the light source intensity. However, a brighter source is more costly, produces extra heat, and requires more careful shielding to prevent stray illumination from reaching the fluorescent detector. In addition, detrimental side effects accompany an increase in light intensity. Undesirable photochemical reactions between the fluorescent dye and protein in the cells may be induced by the more powerful illumination intensity. This distorts the analysis performed and precludes any subsequent study or analysis of the cells after they have been processed through the flow chamber.

An increase in the illumination intensity applied will increase the probability of a photochemical reaction for two reasons. First, the average lifetime in the excited state for the cells of interest in the flow chamber is increased, resulting in a greater possibility of collision between the excited particle with another molecule during this time. Consequently, the rate of undesired chemical reactions increases. In addition, except for rare instances in which there is a 100% conversion of the increased level of stimuli upon the particle of interest, the increased stimuli will tend to heat the cell, and thereby further promote undesired chemical reations.

Accordingly, utilization of the present invention provides a means to obtain increased signal-to-noise ratio from the response detector without requiring increased illumination intensity or electrical potential.

BRIEF DESCRIPTION OF THE INVENTION

In one broad aspect, this invention is an apparatus for distinguishing between discrete particles of different materials entrained in a fluid which exhibit distinguishable responses to physical stimulus comprising a narrow channel through which fluid containing entrained particles of material flows, flow regulation means for maintaining a predetermined flow rate through said channel, means for exerting a spatially discontinuous physical stimulus at positions longitudinally spaced at predetermined intervals along said channel on said particles of material entrained in said fluid to elicit separate responses from each particle of material at each of the aforesaid positions which responses collectively comprise a coded response, transducer means for detecting the separate responses from said discrete particles of material at each of the aforesaid positions and for generating corresponding signals, decoding means connected to said transducer means and correlated with the flow rate and the spacing of the aforesaid positions to decode said coded response and to combine into a single decoded signal the separate signals corresponding to the separate responses emanating from each particle of material detected in response to the physical stimulus. Particles of different materials may be classified according to their responses to the physical stimulus.

In another aspect this invention is a method of distinguishing between discrete particles of interest in a fluid comprising: contacting said particles of interest with a fluorescent dye, which will cause them to fluoresce under a beam of light, passing a fluid containing said particles of interest through a transparent flow chamber, exposing said flow chamber to a plurality of transverse beams of light at positions spaced at predetermined intervals along the length of said flow chamber to elicit coded signals from particles of interest in the form of discrete fluorescent emissions therefrom in response to each beam of light, detecting said coded signals using a transducer producing outputs for each coded signal, decoding said coded signal outputs for individual particles of interest by consolidating the signals to produce a composite output signal for each particle of interest detected, classifying the particles of interest in accordance with differences in the composite output signals, and quantitatively tabulating the particles of interest according to the classifications selected. A method of treating the particles of interest with an appropriate dye is explained in U.S. Pat. No. 3,819,270.

A further specialized application of the present invention involves the application of a plurality of physical stimuli, such as light beams of different wavelength, to the particles of interest. Multiple physical stimuli may be applied to the particles, either simultaneously or sequentially, using one or more code functions to produce multiple responses from appropriate transducers. These transducer outputs are decoded with appropriate decoding means to provide multiple signals from a single particle. Such signals may be combined in appropriate combinations and/or ratios so as to provide means of classifying the sample particles based on the outcomes of these combinations and ratios. A technique for the use of light beams of different wavelength to produce a variety of combined responses in order to identify several classes of particles is set forth in U.S. Pat. No. 3,822,095.

The invention may be more clearly understood by reference to the accompanying illustrations.

DETAILED DESCRIPTION OF THE INVENTION

In a conventional photoanalytic device suitable for determining the extent to which cells of different types are present in a given blood sample, the cells are made to flow one by one through a small capillary tube which is illuminated by imaging a bright source of light through a microscope objective lens. A single beam of light passes transversely through the capillary tube. By appropriately designing the optics, it is possible to obtain a uniformly illuminated region within the capillary tube so that when a single cell passes through this region, the fluorescent light output appears as a single output pulse. The amplitude of the pulse will vary depending upon the extent to which the cell within the region of illumination has absorbed fluorescent dye.

In a typical application of such a conventional photoanalytic device, analysis is performed by taking a differential white cell count of a blood sample. Prior to analysis, the blood is mixed with a fluorescent stain as explained in detail in U.S. Pat. No. 3,819,270. The different types of white cells will absorb differently the amounts of stain, and will therefore yield fluorescent emissions of varying intensity or wavelength when illuminated under a fluorescent microscope. It is thereby possible to perform a similar analysis by passing the cells sequentially through a narrow flow chamber, as described previously, and to determine which type of cell is passing through the capillary tube by noting the amplitude of the pulse received from the photodetector. This pulse amplitude from the photodetector is directly proportional to the strength of the fluorescent emission from the cell which is passed to the photodetector.

Figure 1:
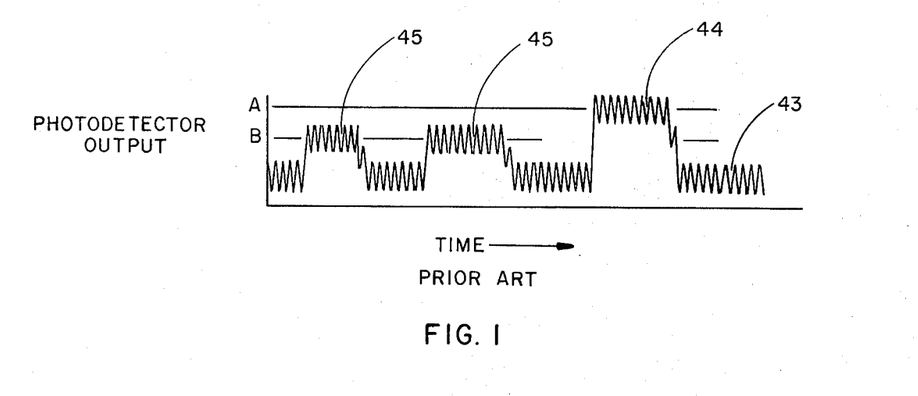
FIG. 1 illustrates typical photodetector response to a plurality of individual cells in a conventional photoanalytic detector.

Over a period of time the photodetector output in a differential white cell counter using a conventional photoanalytic device will be similar to that depicted in FIG. 1. From FIG. 1, the passage of three cells sequentially through the flow chamber is noted. The first two cells responded to the beam of illumination by fluorescing and producing photodetector outputs 45 of amplitude level B during the periods of time indicated. The final cell which was detected responded by producing a photodetector output 44 of a greater amplitude A. Between detected cells, an ambient noise level indicated as 43 prevailed.

Figure 2:
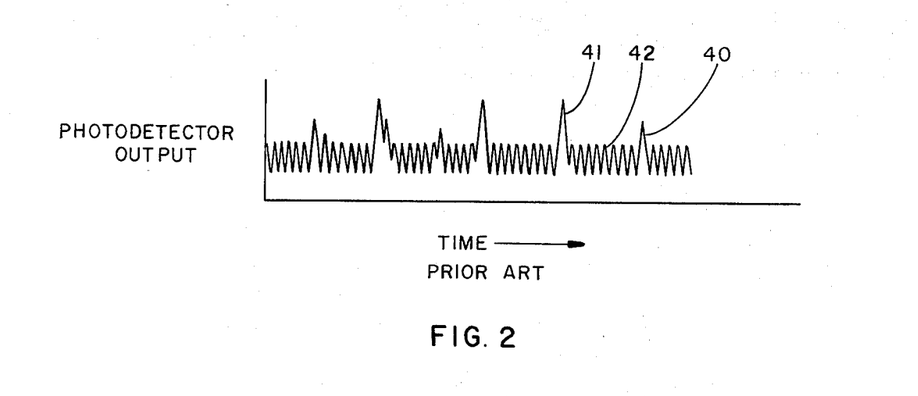
FIG. 2 illustrates photodetector response to a plurality of individual cells in a conventional photoanalytic detector in which the flow rate has been increased.

From FIG. 1 it can be seen that it is possible, using conventional techniques, to count the number of cells producing detector outputs of amplitude A separately from the number of cells producing photodetector outputs of amplitude B. The difference in cell count is useful for medical diagnostic purposes. It should be pointed out, however, that only a limited flow rate through the capillary tube can be achieved with conventional cell counters. If the flow rate is increased above an upper limit, the detector becomes insensitive to the different types of cells passing through the capillary tube. The detector output in such a situation is illustrated in FIG. 2. In FIG. 2, it is virtually impossible to distinguish between cells of one type producing photodetector pulses 41 and cells of another type producing photodetector responses 40. This is because the presence of noise (indicated by the numeral designation 42 in FIG. 2) makes it difficult to determine which type of cell is present unless the output pulse is long enough in duration so that an accurate estimate of its average value can be obtained. This requires the length of the illuminated region in the flow chamber and the velocity of the cells through this region be adjusted relative to each other in order to obtain the necessary pulse duration. To obtain discrimination between the two cell types at a higher flow rate, it is necessary to increase the amplitude of the fluorescent output signals in some manner so that the fluorescent signal differential becomes more pronounced. The most obvious solution is to simply increase the source intensity. As previously explained, however, this is not practical because of the attendant increase in probability of photochemical reaction. Using the pulse coded technique of the present invention, however, it is possible to increase signal-to-noise ratio without increasing illumination intensity.

If instead of a uniformly illuminated region the flow chamber contains a much longer, randomly structured region of illumination in which a plurality of beams of light pass transversely through the flow chamber at fixed positions spaced longitudinally at predetermined invervals along the length of the flow chamber, a cell passing through the flow chamber will produce a different response. More specifically, a cell passing through the flow chamber will produce a series of short pulses as in FIG. 7, instead of the single long pulse. These pulses occur whenever the cell passes through one of the several beams of light. The illumination pattern of the beams of light is so structured that there is a uniquely defined centroid which may be located even if the output signals from sequential particles partially overlap. The illumination pattern formed by the plurality of light beams may be considered to be a code that is employed in the present invention. The illumination pattern of FIG. 7 is merely an illustrative example, and it will be recognized by those skilled in the art of signal detection theory that the embodiment described incorporates the techniques of pulse code transmission and matched filter signal detection; therefore several other possible code patterns exist and are well known.

Figure 4:
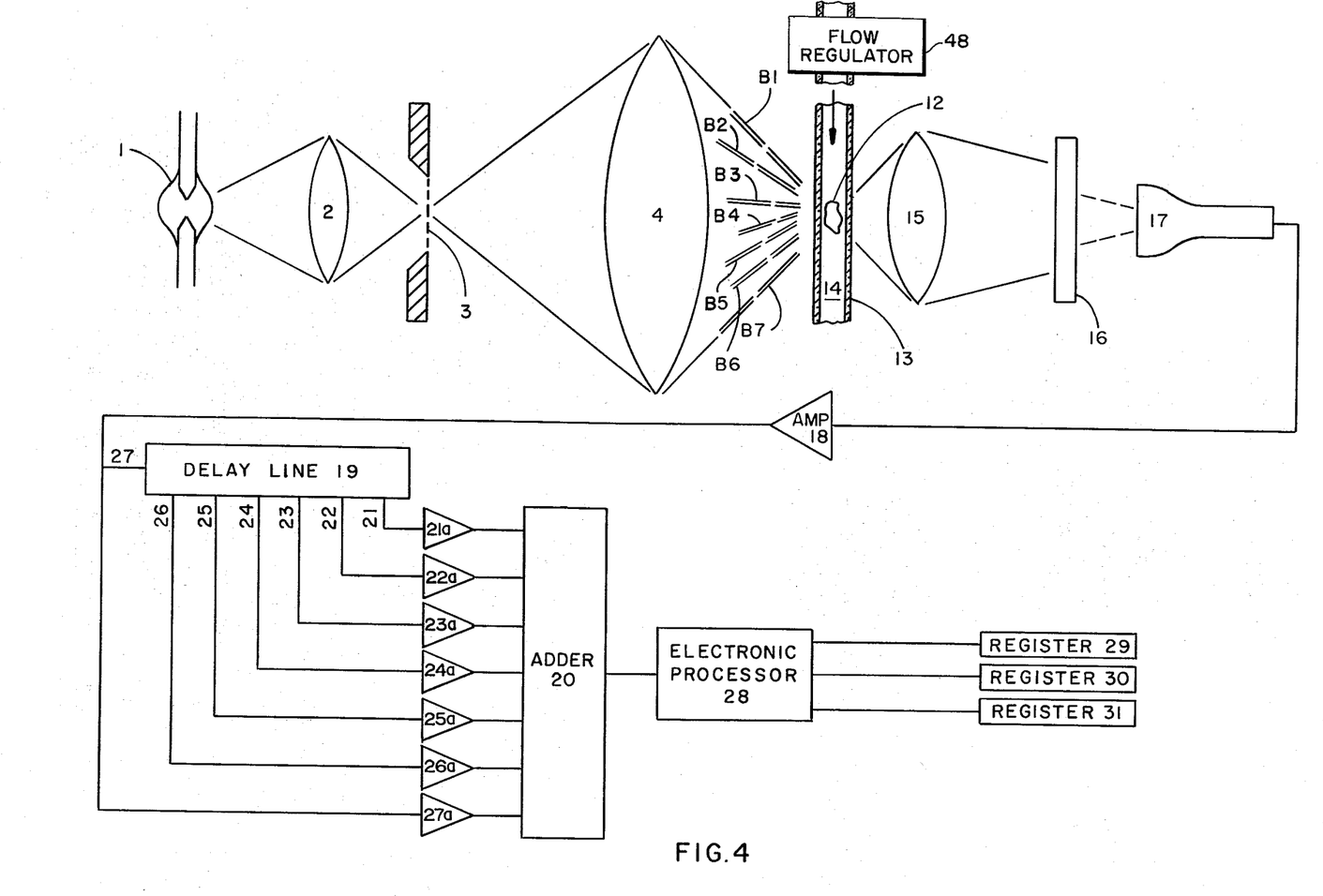
FIG. 4 illustrates an apparatus constructed according to the present invention.
Figure 7:
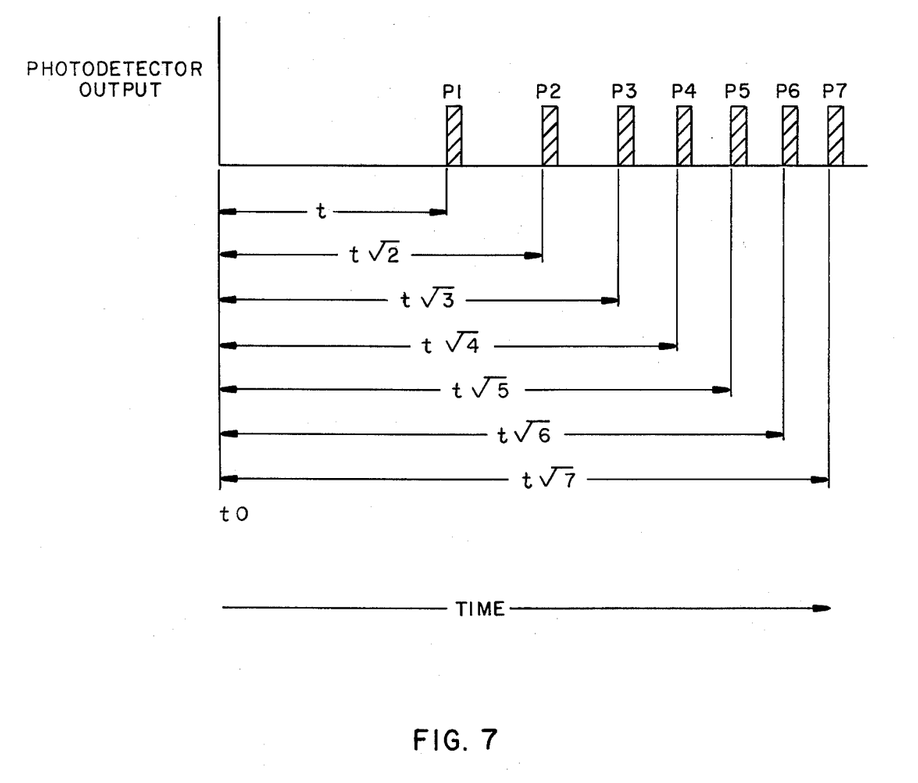
FIG. 7 illustrates the ideal photodetector output from a single cell of interest utilizing the present invention.

The embodiment of FIG. 4 is designed to produce the photodetector response illustrated in FIG. 7. A light source 1 which may be an arc lamp, laser, or other sufficiently bright source, is imaged by an appropriate condensor lens 2 to provide uniform illumination of a coding mask 3. This mask contains the code function as a transmission pattern. Microscope objective lens 4 forms a minified image of the mask 3 in the flow chamber or channel 14 formed by the capillary tube 13. The flow channel 14 is of sufficiently narrow width that discrete particles, such as the cell 12, are forced to flow in single file. Were this not the case, coincident signals would occur which would confuse the processing of data. The mask 3 results in the production of a plurality of beams of light B1 through B7. These beams, B1 through B7, pass transversely through the flow chamber 14 at fixed positions spaced longitudinally at predetermined intervals along the length of the flow chamber. As a single cell 12 passes in the direction of flow indicated by the arrow in FIG. 4, it first encounters the beam B1. When illuminated by beam B1, the cell 12 emits a fluorescent output which produces a photodetector response P1 as in FIG. 7. By the same token, beam B2 produces photodetector response P2, beam B3 produces response P3, and so on. It is to be understood that suitable flow rate regulation means 48 of conventional design maintains a constant flow rate through the channel 14.

The fluorescent light output of FIG. 7 is collected by a second microscope objective lens 15 and is conveyed to a photodetector in the form of a photomultiplier tube 17. The presence of a blocking filter 16 prevents direct light from the source 1 from passing to the photomultiplier 17. The blocking filter 16 interposed between the flow chamber 14 and the photodetector 17 selectively blocks the passage of light from the beams B1 through B7, and preferentially passes light produced by fluorescense of the cell 12 in the fluid stream in the flow chamber 14. Blocking occurs because the fluorescent output in the form of pulses P1 through P7 is at a wavelength different from that of the beams B1 through B7. Blocking filter 16 is selected to allow the passage of light of the same wavelength as the fluorescent emissions, but to block light having a wavelength corresponding to that of direct light transmission from the light source 1. Alternatively, in the case of fluorescent emission, blocking of the illumination beam may be effectively accomplished by orienting the detector perpendicular to the propagation axis of the illumination light in a plane which is both transverse to the direction of flow in the flow cell and which also contains the propagation axis of the illumination light. In FIG. 4, the decoding means is in the form of a delay line 19 with delay line taps and amplifiers 21 through 27 feeding into an addition circuit 20. The output signals from the decoder are conveyed to an electronic processor 28 which counts and classifies the cells in the desired manner and stores the tabulated counts of the particles of interest according to the classifications selected in the registers 29, 30 and 31.

Figure 6:
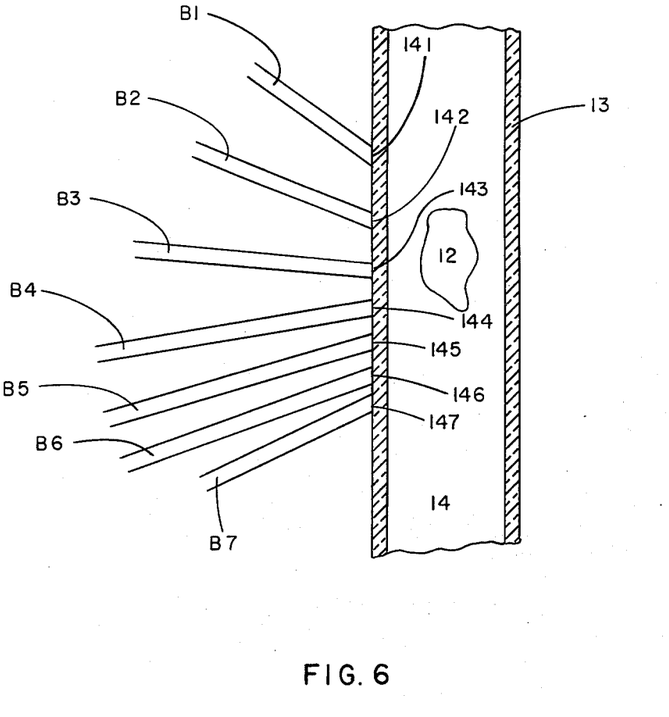
FIG. 6 is an enlarged view of a portion of FIG. 4.

In the embodiment of the apparatus of the invention illustrated, the mask 3 is interposed between the flow chamber 14 and the light source 1 and has apertures spaced therein at coded intervals to allow the beams of light B1 through B7 to emanate from the apertures and strike the flow chamber 14 at predetermined spaced positions 141 through 147 as illustrated in FIG. 6. In the embodiment illustrated, the spacing between adjacent light beams decreases proceeding in the direction of the flow. More specifically, the distance between successive beams is determined by taking the difference of the square roots of their respective numbers in the sequence and multiplying by a scale factor. Thus the first and second beams are spaced by $\sqrt{2} - \sqrt{1}$ times the scale factor, the second and third are spaced by $\sqrt{3} - \sqrt{2}$ times the scale factor and so forth. From this pattern of spacing of the beams B1 through B7, it can be seen that for a constant flow rate through the flow chamber 14, a single cell, 12, will produce from detector 17 a train of output pulses as shown in FIG. 7. These pulses are amplified by amplifier 18, and then passed to delay line 19.

Delay line 19 has N-1 taps, where N is the number of pulses in the code. These taps have respective delays which correspond to the spacing between illumination beams B6 and B7, B5 and B6, and so forth. In other words, for a general code, the taps on the delay line produce a delay which corresponds to the pulse spacing obtained by running the code train backwards in time. These outputs, from delay line 19, are passed to amplifiers as indicated, and the outputs of the lines 21–27 and their associated amplifiers 26–27a are passed to adder circuit 20. The decoding means of the invention is thereby correlated with the spacing of the beam position. It should be noted that no artificial delay exists on line 27.

The operative effect of the lines 21 through 27 is best illustrated by reference to the contents of the adder circuit 20 depicted in FIG. 8. For a cell 12 passing through the flow channel 14, a series of pulses is generated as illustrated in FIG. 7 and as previously explained. By virtue of the line 27 and the delay line taps 21 through 26, each of the pulses P1 through P7 is replicated 7 times. Exemplary delays and pulse arrival times are indicated on the abscissa of FIG. 8. The replication of the pulse P1 from line 27 is the first pulse to reach the adder circuit 20. The pulse P1 from delay line tap 26 is the second pulse to reach the adder circuit 20. The pulses P2 from line 27 and P1 from line 25 reach the adder circuit 27 almost simultaneously to produce a small voltage spike 36 in FIG. 9. It should be noted, however, that no more than a maximum of two pulses are received simultaneously by the adder 20 until time $T_s$ in FIG. 8. At time $T_s$, the pulses P1 from line 21, P2 from line 22, P3 from line 23, P4 from line 24, P5 from line 25, P6 from line 26, and P7 from line 27 all coincide in time. The result is a very large pulse spike 35 as indicated in FIG. 9. Spike 35 is much greater than the smaller spikes 36 produced by incidental coincidences of simultaneous pulses, such as the pulse P1 from line 25, and pulse P2 from line 27 as previously noted.

Figure 8:
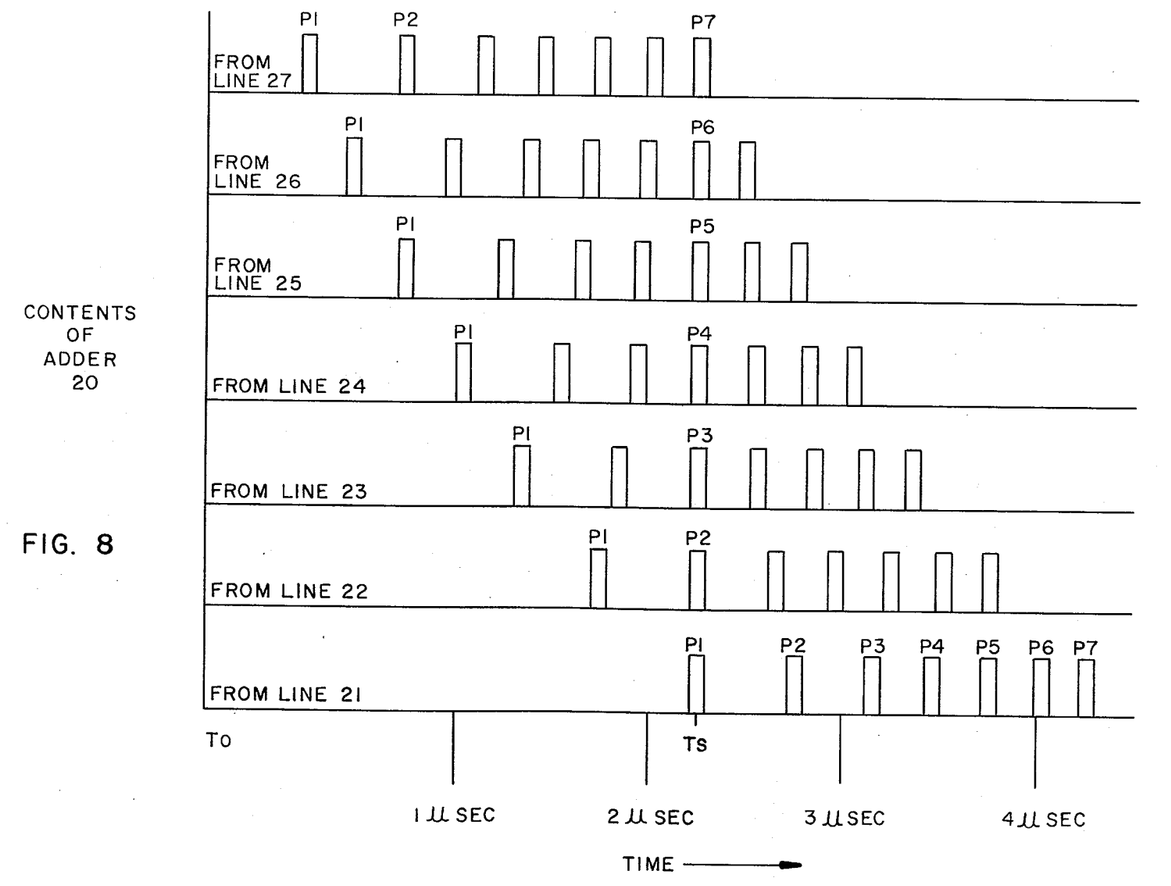
FIG. 8 graphically depicts the manner in which the coded signal of the present invention is decoded.
Figure 9:
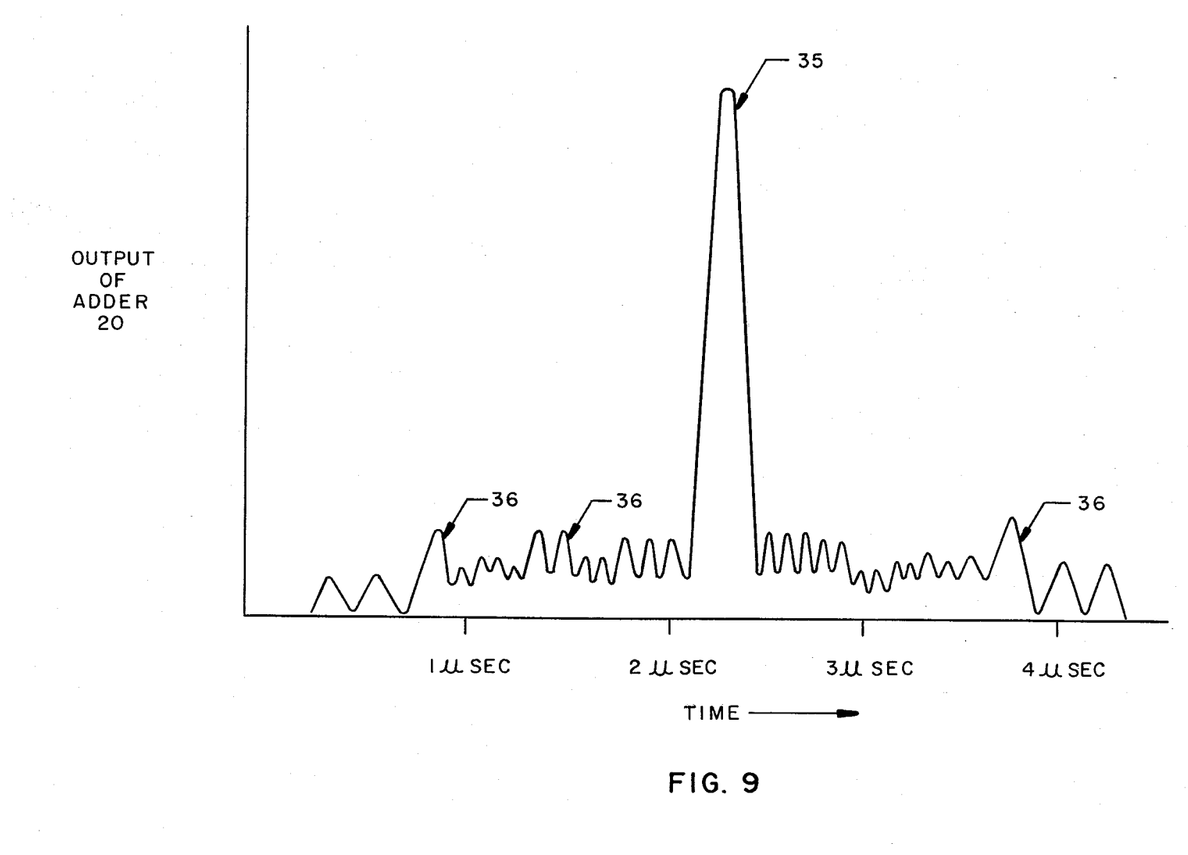
FIG. 9 graphically depicts the output of the decoding device of the present invention.

The decoding of the contents of the adder circuit 20 in FIG. 8 to produce the adder output of FIG. 9 is known as autocorrelation. Using autocorrelation, the response of the decoder has a single narrow voltage peak 35 with a position in time determined by the centroid in time of the original code. The total signal strength of this peak 35 depends upon the number of pulses in the code which is controlled by the length of the flow chamber 14, while the width of the peak depends upon the width of the beams B1 through B7. These two parameters are essentially independent of each other. Thus, successive particles 12 proceeding through the capillary tube 13 need only be separated sufficiently so that the narrow peaks of their autocorrelated output signals do not overlap, and the flow chamber may be increased to any desired length, subject to other practical limitations, in order to obtain sufficient signal strength for the desired particle discrimination.

The code employed in the invention is carefully chosen so that no more than 2 pulses (such as pulse P1 from line 25 and pulse P2 from line 27) coincidentally overlap at any time. The peak amplitude or signal strength of the voltage spike 35 from adder circuit 20 is proportional to the number of pulses in the code. That is, voltage spike 35 (unamplified) would have an amplitude seven times as great as any single one of the pulses in FIG. 7.

Figure 3:
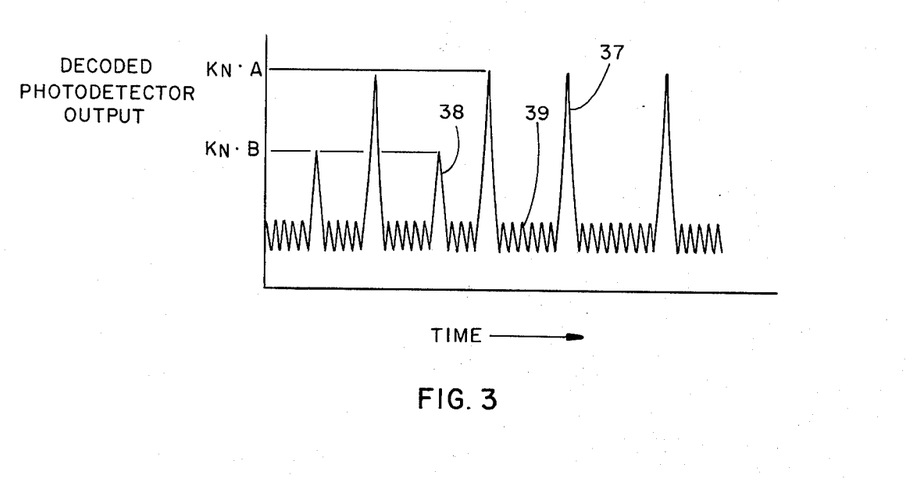
FIG. 3 illustrates a photodetector plus decoding means output at the flow rate of FIG. 2 using the techniques of the present invention.

The decoded photodetector output over a period of time is illustrated in FIG. 3. FIG. 3 represents the response of the device to the passage of several sequential cells of different types through the capillary tubes 13. The flow rate employed with the device of the present invention to achieve the output of FIG. 3 is approximately the same as that used to produce the photodetector output of FIG. 2, which employs a conventional apparatus. It can be seen that contrary to the output of FIG. 2, the output of FIG. 3 can be resolved so that cells of a type A producing pulse spikes 37 can be distinguished from pulses of a type B producing lower amplitude pulse spikes 38. The amplitude of spikes 37 is equal to $K_n \cdot A$, while the amplitude of spike 38 is equal to $K_n \cdot B$, where $K_n$ is a number greater than 1 and is proportional to the number of pulses in the code. A and B are the same amplitudes depicted in FIG. 1.

Figure 5:
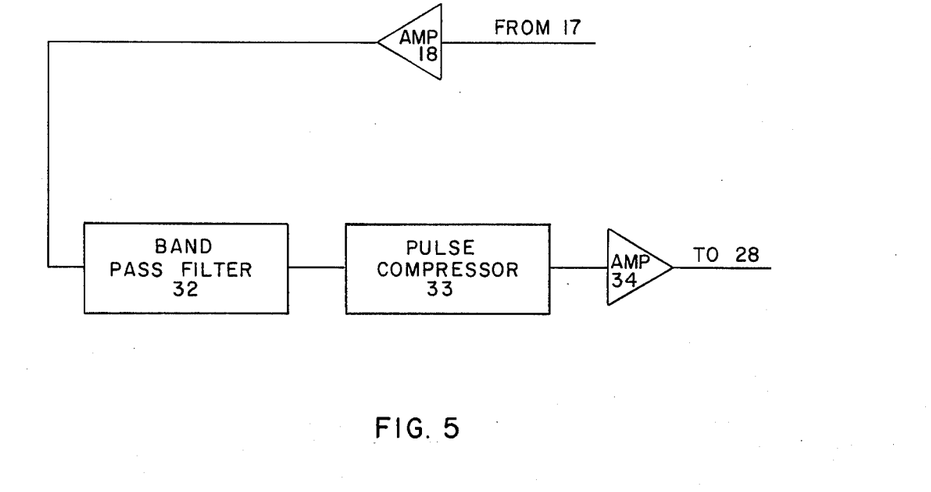
FIG. 5 illustrates an alternative embodiment of a portion of the apparatus of FIG. 4.

While the apparatus depicted in FIG. 4 is probably the preferred construction of the invention, an alternative form of the decoding means is illustrated in FIG. 5. Codes that contain multiple orders, such as a square wave F.M. "chirp," can be designed so that the multiple orders do not overlap in frequency. In this case a decoding device can be constructed by passing the detector output signal from the amplifier 18 through a band pass filter 32 which selects one of the orders, usually the fundamental order. The output from the band pass filter 32 may be passed through a pulse compression means 33 in the form of a dispersive delay line to produce autocorrelated output signals for individual particles. The low pass filter 32 blocks high frequency output, including most noise, from the photomultiplier 17 but passes low frequency outputs such as the pulses P1 through P7. That is, the pulse compression means 33 produces a signal proportional to an integrated sum of the pulses P1 through P7 for a particular particle or cell 12 in the flow channel 14, which signal is passed to an amplifier 34.

In either embodiment, the electronic processor 28 forms a signal classification means for classifying the decoded output signals according to preselected pulse amplitude ranges. The electronic processor 28 also serves as a pulse tabulating means for counting the number of decoded output signals in each selected classification, and for tabulating these counts in the registers 29, 30 and 31. In this way, different types of particles of interest having definitely identifiable fluorescent characteristics may be tabulated separately.

There are a number of different operating conditions under which flow cells employing the pulse coding technique of the present invention demonstrate significant advantages over conventional flow cell arrangements. Conversely, there are some adverse conditions for flow cell measurement in which the use of this invention is not likely to produce an improvement, although neither will it exhibit inferior performance. Specifically, the pulse coded flow cell technique described herein produces a distinct advantage where particle discrimination is based on the outcome of several different measurements, for example, multiple fluorescence measurements, and it is desired to use a single detector for observing all measurements. In this instance several measurements may be desired, for example fluorescence at different wavelengths, on each particle. The standard way of doing this is to image separate channels into the flow cell for each wavelength, and then image the output of each channel, thru isolation filters, to a separate detector. If instead, a set of orthogonal code words are utilized, then they can be imaged into the flow chamber in an overlapping pattern. The output signals can then go to a single detector, without the need of isolation filters, and the subsequent signals can be separated by the orthogonality property. Of course, it is necessary that there be no interaction, such as internal energy transfer, from simultaneous excitation of the different fluorescent mechanisms. Alternatively, the same code word could be used for each channel, and simply imaged into the flow cell with a slight offset between channels. By time gating with one extra detector, it should be possible to separate the output signals for each channel.

This invention is also particularly advantageous where there is insufficient signal because of source or thermal detector noise. There is a definite gain in signal-to-noise from using pulse code techniques. The signal power per unit bandwidth is increased with increasing length of the pulse train, while the noise power per unit bandwidth remains constant.

Flow cell measurement may be desired under conditions where there is essentially no noise, but the signal is a small change from a high bias level which may drift slowly in time. If the pulse is short, and reasonably intense, then a simple AC coupling of the detector output may be adequate for separation of signal from background. If, however, the signal pulse is not sufficiently intense, the only to increase signal energy is by means of time integration. This results in two disadvantages; first the count rate is lowered, and second, a simple AC coupled detector is no longer feasible for separating signal from background. By using a pulse code technique, the desired signal can be made to appear as a wideband signal centered about an offset carrier frequency, thus allowing both a high count rate, and easy separation of signal from background. If the signal occurs as a short pulse, then a simple AC coupled detector may be adequate. If the signal must be kept long and detected by means of time integration, then the use of a pulse coded technique allows both a high count rate and easy separation of signal and background.

On the other hand, no significant advantage is realized by employing pulse coded techniques where there is insufficient signal because of quantum limitations. This may occur where a background level is present or where single pulses from individual particles are quantum limited, but background is essentially non-existent. In the former case there is no gain in signal to noise ratio using pulse coded techniques, while in the latter case the signal to noise gain depends upon the count rate. At the maximum possible count rate, there is essentially no gain using pulse coded techniques, since the constant stream of particles adjacent to the one of interest appears as a noise producing background.

Similarly, there is no particular advantage to pulse coded techniques where the signal tends to vary because of changing particle position or orientation during the time it is in the flow chamber.

However, if the pulse train can be made long enough for a good average on particle orientation to be obtained, then there is some gain in signal-to-noise, especially in combination with detector or source noise. In addition, there is the advantage of easy separation of signal and background compared to a method which simply integrates in one long pulse.

Combinations of the foregoing conditions are of course possible, and the advantage, if any, of using a pulse code technique would essentially be determined by that member of the combination which tends to give the smallest gain.

The form of the invention depicted has been given for purposes of illustration only. Other forms of the device and the techniques in the practice of a method may be utilized to measure scattered light, absorption, or combinations of scattering absorption and fluorescence. In addition, other properties besides optical characteristics may be measured with appropriate instruments. These properties would include electronic charge, dialectric polarization, or electrical conductivity. The embodiments of this invention for measuring such characteristics would necessarily include appropriate modifications in the flow chamber, form of stimulation of a signal dependent upon the desired characteristic, and means for detecting the signal so produced.

I claim:

1. An apparatus for distinguishing between discrete particles of different materials entrained in a fluid which exhibit distinguishable responses to physical stimulus comprising a narrow channel through which fluid containing entrained particles of material flows, flow regulation means for maintaining a predetermined flow rate through said channel, means for exerting an aperiodic spatially discontinuous physical stimulus pattern at positions longitudinally spaced at predetermined intervals along said channel on said particles of material entrained in said fluid to elicit separate responses from each particle of material at each of the aforesaid positions which responses collectively comprise a coded response, transducer means for detecting the separate stimulus responses from said discrete particles of material at each of the aforesaid positions and for generating corresponding signals, decoding means comprising a matched filter for the aforesaid stimulus responses connected to said transducer means and correlated with the flow rate and the spacing of the aforesaid positions to decode said coded response and to combine into a single decoded signal the separate signals corresponding to the separate responses emanating from each particle of material detected in response to the physical stimulus.

2. An apparatus for distinguishing between discrete particles of different materials entrained in a fluid which exhibit distinguishable responses to physical stimulus comprising a narrow channel through which fluid containing entrained particles of material flows, flow regulation means for maintaining a predetermined flow rate through said channel, means for exerting a spatially discontinuous physical stimulus at positions longitudinally spaced at predetermined intervals along said channel on said particles of material entrained in said fluid to elicit separate responses from each particle of material at each of the aforesaid positions which responses collectively comprise a coded response, transducer means for detecting the separate responses from said discrete particles of material at each of the aforesaid positions and for generating corresponding signals, decoding means comprising a band pass filter connected to the transducer output and pulse compression means connected to the aforesaid band pass filter to produce a decoded signal of amplitude proportional to the cumulative amplitude sum of signals emanating from said band pass filter and correlated with the flow rate and the spacing of the aforesaid positions to decode said coded response and to combine into a single decoded signal the separate signals corresponding to the separate responses emanating from each particle of material detected in response to the physical stimulus.

3. An apparatus for use in detecting the presence of particles of interest in a fluid which are treated to fluoresce under the influence of a beam of light comprising: a transparent, narrow flow chamber having a length significantly greater than its width, a means for directing a plurality of beams of light transversely through the flow chamber at fixed positions spaced longitudinally at predetermined intervals along the length of said flow chamber, means for maintaining a constant flow rate of the fluid to be analyzed through said flow chamber, photodetector means viewing said flow chamber and generating electrical pulses in response to detected light emissions, blockiing filter means interposed between said flow chamber and said photodetector means at the aforesaid spaced positions for selectively blocking the passage of light directly emanating from said beams of light and preferentially passing light produced by fluorescence of the aforesaid particles of interest in the fluid to be analyzed in said flow chamber, and decoding means correlated with the aforesaid constant flow rate and the intervals between the aforesaid spaced positions connected to said photodetectors to produce decoded output signals indicative of the cumulative light output from fluorescence of particles of interest passing through said flow chamber.

4. The apparatus according to claim 3 wherein said decoding means comprises a pulse delaying means connected to the output of said photodetector means, separate output lines respectively corresponding to a single one of said fixed positions along said flow chamber wherein a period of delay is associated with each output line, each such period being proportional to the location of the associated position in the sequence of positions encountered by particles of interest in fluid passing through said flow chamber.

5. The apparatus according to claim 3 wherein said means for directing a plurality of beams of light is comprised of a single light source and a mask interposed between said flow chamber and said light source and having apertures spaced therein at coded intervals to allow the aforesaid beams of light to emanate from said apertures and strike said flow chamber at the aforesaid spaced positions.

6. The apparatus of claim 3 further comprising signal classification means for classifying said decoded output signals according to preselected pulse amplitude ranges, and pulse tabulating means for counting the number of decoded output signals in each selected classification, whereby different types of particles of interest having identifiable fluorescence characteristics may be tabulated separately.

7. An apparatus for distinguishing between discrete particles of different materials entrained in a fluid which exhibit distinguishable responses to different physical stimuli comprising a narrow channel through which fluid containing entrained particles of material flows, flow regulation means for maintaining a predetermined flow rate through said channel, means for exerting a plurality of spatially discontinuous physical stimuli at positions longitudinally spaced at predetermined intervals along said channel on said particles of material entrained in said fluid to elicit separate responses from each particle of material at each of the aforesaid positions which responses to each physical stimulus collectively comprise a coded response to that stimulus, transducer means for detecting the separate responses to said stimuli from said discrete particles of material at each of the aforesaid positions and for generating corresponding signals which differ according to the associated stimulus, decoding means connected to said transducer means and correlated with the flow rate and the spacing of the aforesaid positions to decode each of said coded responses and to combine into a single decoded signal the separate signals corresponding to the separate responses emanating from each particle of material detected in response to each physical stimulus.

8. The apparatus of claim 7 wherein said transducer means is constructed to further combine all of the aforesaid separate signals corresponding to the separate responses to all of said stimuli from each particle of material detected to produce a distinguishing composite signal for the associated material.

9. A method of distinguishing between discrete particles of interest in a fluid comprising: contacting said particles of interest with a fluorescent dye which will cause them to fluoresce under a beam of light, passing a fluid containing said particles of interest through a transparent flow chamber, exposing said flow chamber to a plurality of transverse beams of light at positions spaced at predetermined intervals along the length of said flow chamber to elicit coded signals from particles of interest in the form of discrete fluorescent emissions therefrom in response to each beam of light, detecting said coded signals using a transducer producing outputs for each coded signal, decoding said coded signal outputs for individual particles of interest by consolidating the signals to produce a composite output signal for each particle of interest detected, classifying the particles of interest in accordance with differences in the composite output signals, and quantitatively tabulating the particles of interest according to the classifications selected.

10. The method of claim 8 wherein the coded signal outputs are delayed for an interval of time proportional to the relative longitudinal position along the flow chamber of the beam of light associated therewith.

11. A method of distinguishing between discrete particles of interest in a fluid comprising: contacting said particles of interest with a fluorescent dye which will cause them to fluoresce under a beam of light in a manner determined by the wavelength of the light, passing a fluid containing said particles of interest through a transparent flow chamber, exposing said flow chamber to a plurality of transverse beams of light of different wavelengths at positions spaced at predetermined intervals along the length of said flow chamber to elicit coded signals from particles of interest in the form of fluorescent emissions therefrom in response to each beam of light and distinguished by the wavelength thereof, isolating and detecting said coded signals using a transducer producing outputs for each coded signal, decoding said coded signal outputs for individual particles of interest by consolidating the signals to produce a composite output signal for each particle of interest detected, classifying the particles of interest in accordance with differences in the composite output signals, and quantitatively tabulating the particles of interest according to the classifications selected.

12. The method of claim 11 wherein beams of light of different wavelength are concurrently applied to said particles.

13. The method of claim 11 wherein beams of light of different wavelength are successively applied to each of said particles.

* * * * *